United States Patent
Ciccognani et al.

(10) Patent No.: US 7,854,940 B2
(45) Date of Patent: Dec. 21, 2010

(54) BROAD SPECTRUM PRESERVATION BLENDS

(75) Inventors: Diana T. Ciccognani, Cheshire, CT (US); Kevin N. DiNicola, Wolcott, CT (US); Stephen D. Hinden, Hillsdale, NJ (US); Katherine P. Roberts, Derby, CT (US)

(73) Assignee: Arch Chemicals, Inc., Norwalk, CT (US)

( * ) Notice: Subject to any disclaimer, the term of this patent is extended or adjusted under 35 U.S.C. 154(b) by 1408 days.

(21) Appl. No.: 11/224,397

(22) Filed: Sep. 12, 2005

(65) Prior Publication Data

US 2006/0057175 A1    Mar. 16, 2006

Related U.S. Application Data

(60) Provisional application No. 60/610,772, filed on Sep. 16, 2004.

(51) Int. Cl.
*A01N 25/00*    (2006.01)
*A61K 8/00*    (2006.01)
*A61K 9/00*    (2006.01)

(52) U.S. Cl. .................... 424/404; 424/400; 424/405

(58) Field of Classification Search .................... None
See application file for complete search history.

(56) References Cited

U.S. PATENT DOCUMENTS

| | | | |
|---|---|---|---|
| 5,708,023 A * | 1/1998 | Modak et al. | 514/494 |
| 5,733,362 A | 3/1998 | Hahn | |
| 6,447,793 B2 * | 9/2002 | Aust et al. | 424/405 |
| 6,607,738 B2 | 8/2003 | Salmon et al. | |
| 6,696,048 B2 | 2/2004 | Karpov et al. | |
| 6,784,145 B2 * | 8/2004 | Delambre et al. | 510/130 |
| 7,342,044 B2 * | 3/2008 | Lutz | 514/460 |
| 2003/0082129 A1 * | 5/2003 | Buckingham et al. | 424/70.12 |
| 2005/0106191 A1 | 5/2005 | Kobayashi et al. | |
| 2005/0182142 A1 | 8/2005 | Kobayashi et al. | |
| 2005/0222276 A1 | 10/2005 | Schmaus et al. | |
| 2005/0228032 A1 | 10/2005 | Merianos et al. | |

FOREIGN PATENT DOCUMENTS

| | | |
|---|---|---|
| EP | 1206933 A | 5/2002 |
| EP | 1238651 A | 9/2002 |
| WO | WO98/47469 | 10/1998 |

\* cited by examiner

*Primary Examiner*—Lakshmi S Channavajjala
(74) *Attorney, Agent, or Firm*—Dale L. Carlson; Wanli Wu; Wiggin and Dana LLP

(57) ABSTRACT

A composition having effective broad spectrum preservation activity comprising a mixture of caprylyl glycol or one or more analogs thereof, or mixtures thereof with a preservative selected from the group consisting of: (1) chloroxylenol and 2-phenoxyethanol, (2) chloroxylenol and chlorphenesin, (3) chlorphenesin and 2-phenoxyethanol, and (4) chloroxylenol, chlorphenesin and 2-phenoxyethanol.

7 Claims, No Drawings

US 7,854,940 B2

BROAD SPECTRUM PRESERVATION BLENDS

CROSS-REFERENCE TO RELATED CASES

This utility patent application claims the benefit of U.S. Provisional Patent Application Ser. No. 60/610,772 entitled "Broad Spectrum Preservation Blends" that was filed on Sep. 16, 2004. That provisional patent application is incorporated herein by reference in its entirety.

BACKGROUND OF THE INVENTION

1. Field of the Invention

The present invention relates to broad spectrum preservative blends. In particular, the present invention relates to broad spectrum preservative blends that incorporate caprylyl glycol with either chloroxylenol or chlorphenesin or both.

2. Brief Description of Art

Preservatives are commonly used in personal care products. Preservatives are aimed at protecting such products from decay or spoilage, mainly caused by microorganisms. They typically possess anti-microbial activity.

Because preservative agents may cause adverse effects such as allergic responses and skin irritation, it is desirable to use them in the smallest amount possible in the cosmetics or other personal care products. Thus, a balance must be achieved by having an effective anti-microbial amount of the preservative or preservatives in the product, yet having that amount be as small as possible to avoid or reduce the chance of adverse effects. Also, it is desirable that the preservative or blend of preservatives be effective against the widest possible types of potentially harmful microorganisms that could cause decay or spoilage of personal care products. Furthermore, such preservatives should be chemically and physically compatible with the other ingredients in the personal care product.

2-Phenoxyethanol, chloroxylenol and chlorphenesin are all known preservatives for personal care products. Caprylyl glycol is a known moisturizer used in cosmetic preparations and is known to increase the antimicrobial activity of certain preservatives. For example, European Patent Application EP1206933 A1 teaches compositions containing blends of caprylyl glycol or an analog thereof, with a preservation agent. This reference states that the preservation agents may include phenoxyethanol or chloroxylenol. However, the preferred preservative in this reference is iodopropynyl butyl carbonate (IPBC). See paragraphs 20 and 21 on page 3 of this European Patent Application.

The present invention has found that particular triblends and tetrablends that incorporate caprylyl glycol with either (1) 2-phenoxyethanol and chloroxylenol; (2) 2-phenoxyethanol and chlorphenesin; (3) chloroxylenol and chlorphenesin; or (4) 2-phenoxyethanol, chloroxylenol and chlorphenesin exhibit higher broad spectrum antimicrobial preservative effects over the simple diblends disclosed in EP 1,206,933.

BRIEF SUMMARY OF THE INVENTION

Therefore, one aspect of the present invention is directed to a composition having effective broad spectrum preservation activity comprising a mixture of caprylyl glycol or one or more analogs thereof, or mixtures thereof, with a preservative comprising chloroxylenol and 2-phenoxyethanol.

Still another aspect of the present invention is directed to a composition having effective broad spectrum preservation activity comprising a mixture of caprylyl glycol, or one or more analogs thereof, or mixtures thereof, with a preservative comprising chloroxylenol and chlorphenesin.

Still another aspect of the present invention is directed to a composition having effective broad spectrum preservation activity comprising a mixture of caprylyl glycol, or one or more analogs thereof, or mixtures thereof, with a preservative comprising chlorphenesin and 2-phenoxyethanol.

Yet another aspect of the present invention is directed to a composition having effective broad spectrum preservation activity comprising a mixture of caprylyl glycol, or one or more analogs thereof, or mixtures thereof, with a preservative comprising chloroxylenol, 2-phenoxylethanol, and chlorphenesin.

DETAILED DESCRIPTION OF THE INVENTION

As used herein, caprylyl glycol refers to 1,2-octanediol and can be structurally represented by the formula:

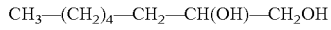

$CH_3—(CH_2)_4—CH_2—CH(OH)—CH_2OH$

Caprylyl glycol analogs comprise $C_{5\text{-}20}$ alkanediols, in particular $C_{6\text{-}16}$ alkanediols, more in particular $C_{6\text{-}12}$ alkanediols. Preferred are the alkanediols mentioned herein wherein the hydroxyl groups are vicinally substituted. Examples of such alkanediols are 2,3-octanediol, 1,2-nonanediol, 1,2-decanediol, 1,2-dodecanediol, 1,2-heptanediol, 1,2-hexanediol, 3,4-octanediol and the like. Of particular interest are those vicinal alkanediols wherein one hydroxyl is substituted at an end carbon and the other on the carbon atom next thereto.

A particular group of caprylyl glycol analogs are those which have a 1,2-octanediol skeleton which is further substituted with 1, 2 or 3 $C_{1\text{-}4}$ alkyl groups (or 1,2-octanediol substituted with 1, 2 or 3 $C_{1\text{-}4}$ alkyl groups) such as, for example, 3-methyl-1,2-octanediol, 4-methyl-1,2-octanediol, 3,4-dimethyl octanediol, 3-ethyl-1,2-octanediol, 4-ethyl-1,2-octanediol and the like.

The caprylyl glycol analogs that can be used in the compositions or formulations of the invention preferably are devoid of any adverse effects on the skin such as allergic reactions and irritation.

The term 'caprylyl glycol or one or more analogs thereof, or mixtures thereof' is also meant to comprise mixtures of caprylyl glycol and one or more of its analogs, or mixtures of two or more caprylyl glycol analogs, in particular those analogs mentioned herein. The term 'caprylyl glycol' when used in isolation is also meant to comprise caprylyl analogs, in particular the analogs mentioned herein. The term 'caprylyl glycol' when used in isolation is also meant to comprise mixtures of caprylyl glycol and one or more caprylyl glycol analogs, or mixtures of two or more caprylyl glycol analogs, in particular those analogs mentioned herein.

"2-Phenoxyethanol" is also known as 1-hydroxy-2-phenoxyethane or ethylene glycol monophenyl ether.

Chloroxylenol is also known as 4-chloro-3, 5-dimethyl phenol.

Chlorphenesin is also known as 3-(4-chlorophenoxy)-1, 2-propanediol.

As used herein the terms 'preservative' and 'preservative agent' of the present invention are meant to comprise either (1) 2-phenoxyethanol and chloroxylenol; (2) 2-phenoxyethanol and chlorphenesin; (3) chloroxylenol and chlorphenesin; or (4) 2-phenoxyethanol, chloroxylenol and chlorphenesin, with or without optional ingredients.

The amount of caprylyl glycol or its analog in the formulations according to this invention may vary, but will be selected such that the combination thereof with the preservative has an effective preservative activity. Preferably, the caprylyl glycol component will constitute from about 5% to about 40% by weight, more preferably, about 10% to about 30% by weight, and most preferably, about 15% to about 25% by weight, based on the sum of the caprylyl glycol component plus preservative agents or agents in the mixture.

If the preservative agent includes both 2-phenoxyethanol with either or both chloroxylenol or chlorphenesin, then the weight ratio of the 2-phenoxyethanol to the chloroxylenol or the chlorphenesin or both is preferably from about 2:1 to about 9:1; more preferably, 2.5:1 to about 6:1, and most preferably, from about 3:1 to 5:1. If the preservative agent includes a mixture of chloroxylenol and chlorphenesin (with or without 2-phenoxyethanol), then the weight ratio of the chloroxylenol to the chlorphenesin is preferably from about 9:1 to about 1:9, more preferably, from about 5:1 to about 1:5, and most preferably, about 3:1 to about 1:3.

One most preferable commercial candidate is a composition comprising 20% by weight caprylyl glycol; 64% by weight 2-phenoxyethanol and 16% by weight chloroxylenol (i.e. 4:1 weight ratio of 2-phenoxyethanol to chloroxylenol). This candidate is referred to as Mikrokill™ PCC. A second preferable commercial candidate is a composition comprising 20% by weight caprylyl glycol; 64% by weight 2-phenoxyethanol and 16% by weight chlorphenesin. This candidate is referred to as Mikrokill™ COS (See MIC Experiments and Tables 5 and 6 below).

The term 'effective preservation activity' means that its activity is such that the composition or formulation is protected for a sustained period of time, in particular during the so-called 'shelf life' of the product. The 'shelf-life' of a product is determined according to methods generally known in the art.

The term "broad spectrum" as used in this specification and claims means a preservative having good preservation properties against a wide spectrum of microorganisms that commonly will decay or spoil personal care products such as cosmetics or non-personal care products.

The compositions of the present invention contain caprylyl glycol and/or an analog thereof and the above-noted preservatives, and optionally other components. These other optional components may be solvents or any of the other components mentioned hereinafter as components that can be added to the topical personal care formulations according to the invention.

The compositions of the present invention are generally prepared by mixing the caprylyl glycol and/or the analog thereof, and the preservative agent or agents. Solvent may be added after mixing, or the components are mixed while being present in a solvent. Other components may be added during the mixing or afterwards. The said caprylyl glycol and preservative may also be added to a premix of other components.

This invention further relates to topical formulations containing a composition as defined herein. Topical compositions comprise as well dermatological formulations (or topical pharmaceutical formulations), as cosmetic formulations. Said topical formulations may further contain other ingredients or additives used in dermatological or in cosmetic formulations, including other active ingredients.

The formulations according to the present invention are formulated into forms that are useful in personal care products, especially in emulsions.

The topical formulations according to the present invention may additionally contain further ingredients or additives such as solvents, surfactants, emulsifiers, consistency factors, conditioners, emollients, skin caring ingredients, moisturizers, thickeners, lubricants, fillers, anti-oxidants, other preservatives, active ingredients, in particular dermatologically active ingredients, fragrances and the like, as well as mixtures thereof. Active ingredients as mentioned herein comprise, for example, anti-inflammatories, anti-bacterials, anti-fungals and the like agents. Active ingredients suited for topical applications are particularly preferred.

Suitable surfactants comprise: alkyl sulfates e.g. sodium lauryl sulfate, ammonium lauryl sulfate; sodium cetearyl sulfate; alkyl sulfoacetates e.g. sodium lauryl sulfoacetate; alkyl ether sulfates e.g. sodium laureth sulfate; sodium trideceth sulfate; sodium oleth sulfate; ammonium laureth sulfate; alkyl ether sulfosuccinates e.g. disodium laureth sulfosuccinate; alkyl glycosides e.g. decyl glucoside; lauryl glucoside; alkyl isethionates amphoterics e.g. cocamidopropyl betaine; sodium cocoamphoacetate; sodium lauroamphoacetate; disodium lauroamphodiacetate; disodium cocoamphodiacetate; sodium lauroamphopripionate; disodium lauroamphodipropionate; potassium or ammonium salts of the aforementioned amphoterics; capryl/capramidopropyl betaine; undecylenamidopropyl betaine; lauromidopropyl betaine; and fatty alcohol polyglycol ethers.

Suitable emulsifiers are e.g. anionics as salts of fatty acids e.g. sodium stearate or sodium palmitate, organic soaps e.g. mono-, di- or triethanolaminoleate, sulfated or sulfonated compounds e.g. sodium lauryl sulfate or sodium cetyl sulfonate, saponines, lamepones; cationics as quaternary ammonium salts; nonionics as fatty alcohols, fatty acid ester with saturated or unsaturated fatty acids, polyoxyethylenesters or polyoxyethylenethers of fatty acids, polymers from ethylene oxide and propylene oxide or propylene glycol, amphotherics as phosphatides, proteins as gelatine, casein alkylamidobetaines, alkyl betaines and amphoglycinates, alkyl phosphates, alkylpolyoxyethylene phoaphates or the corresponding acids, silicone derivatives, e.g. alkyl dimethiconecoplyol.

Suitable consistency factors are e.g. fatty alcohols or their mixtures with fatty acid esters, e.g. acetylated lanolin alcohol, aluminum stearates, carbomer, cetyl alcohol, glyceryl oleate, glyceryl stearate, glyceryl stearate (and) PEG 100 stearate, magnesium stearate, magnesium sulfate, oleic acid, stearic acid, stearyl alcohol, myristyl myristate, isopropyl palmitate, beeswax and synthetic equivalents thereof, carbomers, and the like. Suitable conditioners are e.g. alkylamido ammonium lactate, cetrimonium chloride and distearoylethyl hydroxyethylmonium methosulfate and cetearyl alcohol, cetyl dimethicone, cetyl ricinoleate, dimethicone, laureth-23, laureth-4, polydecene, retinyl palmitate, quaternized protein hydrolysates, quaternized cellulose and starch derivatives, quaternized copolymers of acrylic or methacrylic acid or salts, quaternized silicone derivatives.

Suitable emollients are e.g. cetearyl isononanoate, cetearyl octanoate, decyl oleate, isooctyl stearate, coco caprylate/caprate, ethylhexyl hydroxystearate, ethylhexyl isononanoate, isopropyl isostearate, isopropyl myristate, oleyl oleate, hexyl laurate, paraffinum liquidum, PEG-75 lanolin, PEG-7 glyceryl cocoate, petrolatum, ozokerite cyclomethicone, dimethicone, dimethicone copolyol, dicaprylyl ether, *butyrospermum parkii, buxus chinensis*, canola, carnauba cera, *copernicia cerifera, oenothera biennis, elaeis guineensis, prunus dulcis*, squalane, *zea mays, glycine soja, helianthus annuus*, lanolin, hydrogenated castor oil, hydrogenated coconut oil, hydrogenated polyisobutene, sucrose cocoate, stearoxy dimethicone, lanolin alcohol, isohexadecane.

Suitable skin care ingredients are e.g. plant extracts, bisabolol, anti-inflammatory agents, urea, allantoin, panthenol and panthenol derivatives, phytantriol, vitamins A, E, C, D, ceramides of animal or plant origin, lecithins, and the like.

Suitable moisturizers are e.g. butylenes glycol, cetyl alcohol, dimethicone, dimyristyl tartrate, glucose glycereth-26, glycerin, glyceryl stearate, hydrolyzed milk protein, lactic acid, lactose and other sugars, laureth-8, lecithin, octoxyglycerin, PEG-12, PEG 135, PEG-150, PEG-20, PEG-8, pentylene glycol, hexylene glycol, phytantriol, poly quaternium-39 PPG-20 methyl glucose ether, propylene glycol, sodium hyaluronate, sodium lactate, sodium PCA, sorbitol, succinoglycan, synthetic beeswax, tri-C 14-15 alkyl citrate, starch.

Suitable thickeners are e.g. acrylates/steareth-20 methacrylate copolymer, carbomer, carboxymethyl starch, cera alba, dimethicone/vinyl dimethicone crosspolymer, propylene glycol alginate, hydroxyethylcellulose, hydroxypropyl methylcellulose, silica, silica dimethyl silylate, xanthan gum, hydrogenated butylenes/ethylene/styrene copolymer.

Suitable lubricants are e.g. adipic acid, fumaric acid and its salts, benzoic acid and its salts, glycerine triacetate, sodium or magnesium lauryl sulfate, magnesium stearate, solid polyethylenglycol, polyvinylpyrrolidone, boric acid, mono-laurate or mono-palmitate, myristyl alcohol, cetyl alcohol, cetyl-stearyl alcohol, talcum, calcium or magnesium salts of higher fatty acids, mono-, di- or triglycerides of higher fatty acids, polytetrafluorethylen.

Suitable antioxidants are e.g. sulfites, e.g. sodium sulfite, tocopherol or derivates thereof, ascorbic acid or derivates thereof, citric acid, propyl gallate, chitosan glycolate, cysteine, N-acetyl cysteine plus zinc sulfate, thiosulfates, e.g. sodium thiosulfate, polyphenoles and the like.

The compositions may further contain active ingredients, e.g. anti-microbials, anti-inflammatories, plant extracts, bisabolol, panthenol, tocopherol, actives for anti-stinging, anti-irritant or anti-dandruff applications, or anti-aging agents such as retinol, melibiose and the like. Other suitable actives are e.g. *Medicago officinalis, Actinidia chinensis*, allantoin, *Aloe barbadensis, Anona cherimolia, Anthemis nobilis, Arachis hypogaea, Arnica Montana, Avena sativa*, beta-carotene, bisabolol, *Borago officinalis*, butylenes glycol, *Calendula officinalis, Camellia sinensis*, camphor, *Candida bombicola*, capryloyl glycine, *Carica papaya, Centaurea cyanus*, cetylpyridinium chloride, *Chamomilla recutita, Chenopodium quinoa, Chinchona succirubra, Chondrus crispus, Citrus aurantium dulcis, Citrus grandis, Citrus limonum, Cocos nucifera, Coffea Arabica, Crataegus monogina, Cucumis melo*, dichlorophenyl imidazoldioxolan, *Enteromorpha compressa, Equisetum arvense*, ethoxydiglycol, ethyl panthenol, farnesol, ferulic acid, *Fragaria chiloensis, Gentiana lutea, Ginkgo biloba*, glycerin, glyceryl laurate, *Glycyrrhiza glabra, Hamamelis virginiana*, heliotropine, hydrogenated palm glycerides, citrates, hydrolyzed castor oil, hydrolyzed wheat protein, *Hypericum perforatum, Iris florentina, Juniperus communis, Lactis proteinum*, lactose, *Lawsonia inermis*, linalool, *Linum usitatissimum*, lysine, magnesium aspartate, *Magnifera indica, Malva sylvestris*, mannitol, mel *Melaleuca alternifolia, Mentha piperita*, menthol, menthyl lactate, *Mimosa tenuiflora, Nymphaea alba*, olaflur, *Oryza sativa*, panthenol, paraffinum liquidum, PEG-20M, PEG-26 jojoba acid, PEG-26 jojoba alcohol, PEG-35 castor oil, PEG-40 hydrogenated castor oil, PEG-60 hydrogenated castor oil, PEG-8 caprylic/capric acid, *Persea gratissima*, petrolatum, potassium aspartate, potassium sorbate, propylene glycol, *Prunus amygdalus dulcis, Prunus armeniaca, Prunus persica*, retinyl palmitate, *Ricinus communis, Rosa canina, Rosmarinus officinalis, Rubus idaeus*, salicylic acid, *Sambucus nigra*, sarcosine, *Serenoa serrulata, Simmondsia chinensis*, sodium carboxymethyl betaglucan, sodium cocoyl amino acids, sodium hyaluronate, sodium palmitoyl praline, stearoxytrimethylsilane, stearyl alcohol, sulfurized TEA-ricinoleate, talc, *Thymus vulgaris, Tilia cordata*, tocopherol, tocopheryl acetate, trideceth-9, *triticum vulgare*, tyrosine, undecylenoyl glycine, urea, *Vaccinium myrtillus*, valine, zinc oxide, zinc sulfate.

The combination of caprylyl glycol and/or an analog thereof and a preservative can be used in emulsions (both oil-in-water and water-in-oil), in aqueous solutions, in PIT (phase inversion temperature) emulsions, in oily solutions, in foaming cosmetic formulations (foams), and in so-called multiple emulsions, e.g. in triple emulsions (such as water/oil/water emulsions).

The compositions of the invention can be formulated as creams, gels, liquids or lotions. They can be used in shampoos, hair conditioners, hair dyes, hair preparations, after-shave lotions, bath soaps and detergents, fragrance preparations, sun care products, indoor tanning products, body and hand preparations, personal cleansers, shaving preparations, tonics, dressings and other hair grooming aids, moisturizing preparations, skin care preparations, wipes and the like. These compositions can be also used in a variety of non-personal care products.

The topical formulations of the invention are prepared by adding other ingredients to a composition as defined herein, or addition to a mixture of ingredients a composition as defined herein. Alternatively, said formulations may also be made by mixing the ingredients individually or by group-wise mixing. Subsequently other specific ingredients, such as perfumes, may be added.

In a further aspect, this invention is concerned with synergistic effects between two agents, caprylyl glycol or an analog on the one hand, with the above-noted preservative blends on the other in terms of anti-microbiological activity, as well as anti-microbiological spectrum, that show a better efficacy than the two components alone. Hence in still a further aspect the present invention provides synergistic cosmetic compositions comprising caprylyl glycol and/or an analog and these preservative blends.

The use of caprylyl glycol or one or more analogs thereof, or mixtures thereof in combination with a preservative, in particular of 1,2-octanediol with 2-phenoxyethanol and chloroxylenol or 1,2-octanediol with 2-phenoxyethanol and chlorphenesin, in cosmetic formulations results in broad anti-microbial protection in the container. The anti-microbial protection is against bacteria, fungi, in particular against species such as, for example, *Pseudomonas aeruginosa, Escherichia coli, Staphylococcus aureus, Candida albicans, Aspergillus niger* and the like.

The combinations of the invention are particularly attractive for personal care products.

The present invention is further described in detail by means of the following Examples and Comparisons. All parts and percentages are by weight and all temperatures are degrees Celsius unless explicitly stated otherwise.

EXAMPLES

A. Challenge Test in Broth

Procedure: Preservatives and/or blends as shown in Table 2, were mixed into Tryptic Soy Broth at 0.5% volume to volume. A challenge protocol similar to the CTFA method was followed to assess efficacy against a broad spectrum of microorganisms. The four separate inocula were: *Staphylococcus aureus* (ATCC 6538), *Pseudomonas aeruginosa* (ATCC 9027) and *Enterobacter gergoviae* (cosmetic isolate), *Candida albicans* (ATCC 10231), and mixed molds *Aspergillus niger* (ATCC 6275) and a *Penicillium* sp. cosmetic isolate.

Tubes containing 20 milliliters of broth were inoculated with approximately 1,500,000 bacteria per gram, 50,000 yeast cells per gram or 100,000 mold spores per gram. Individual challenges were prepared from overnight slants of bacteria and yeast cultures and from heavily sporulating mold cultures, 7 to 10 days old. All samples were plated quantitatively for viable organisms after 24 hours and 8 days.

Results: As shown by the results in Table 1, the addition of 20% caprylyl glycol to the 2-phenoxyethanol/chloroxylenol blend greatly improved activity against the gram negative bacteria.

Conclusions: Since gram negative bacteria are common contaminants of aqueous formulations, a preservative blend showing enhanced activity against this group of microorganisms is very desirable.

organisms. The four separate inocula were: *Staphylococcus aureus* (ATCC 6538), *Pseudomonas aeruginosa* (ATCC 9027), *Candida albicans* (ATCC 10231), and mixed molds *Aspergillus niger* (ATCC 6275) and a *Penicillium* sp. cosmetic isolate. Samples (10 grams each) were inoculated with approximately 1,500,000 bacteria per gram, 250,000 yeast cells per gram or 40,000 mold spores per gram. Individual challenges were prepared from overnight slants of bacteria and yeast cultures and from heavily sporulating mold cultures, 7 to 10 days old. All samples were plated qualitatively for viable organisms after 24 hours with quantitative counts made after 1 and 2 weeks.

Results: As shown by the results in Tables 4A and 4B, the addition of caprylyl glycol to the 2-phenoxyethanol/chloroxylenol blend greatly improved activity against the

TABLE 1

Efficacy Of Preservative Blends With And Without Caprylyl Glycol.

| Preservative Blend (added at 0.5% v/v) | Colony Forming Units per Milliliter of Broth (CFU/ml) after 8 Days | | | |
|---|---|---|---|---|
| | *P. aeruginosa* *E. gergoviae* | *S. aureus* | *C. albicans* | *A. niger/ Penicillium* sp. |
| Control - none | $8.0 \times 10^9$ | $1.1 \times 10^9$ | ND | $7.6 \times 10^5$ |
| 2-Phenoxyethanol | $9.1 \times 10^7$ | $3.2 \times 10^8$ | $4.0 \times 10^3$ | $5.8 \times 10^2$ |
| 4:1 ratio of 2-Phenoxyethanol:Chloroxylenol | $2.5 \times 10^4$ | $2.0 \times 10^1$ | $<1 \times 10^1$ | $<1 \times 10^1$ |
| 20% Caprylyl Glycol in 2-Phenoxyethanol | $1.8 \times 10^8$ | $>4 \times 10^6$ | $<1 \times 10^1$ | $4.3 \times 10^2$ |
| 20% Caprylyl Glycol in 4:1 ratio of 2-Phenoxyethanol:Chloroxylenol | $<1 \times 10^1$ | $<1 \times 10^{3*}$ | $<1 \times 10^1$ | $<1 \times 10^1$ |

*= none detected at the lowest dilution tested
ND = Not Determined

TABLE 2

Concentration Of Each Blend Ingredient In Tryptic Soy Broth With 0.5% Addition Of Preservative Blend.

| Preservative Blend | Phenoxy-ethanol | Chloroxylenol | Caprylyl Glycol |
|---|---|---|---|
| Control - none | None | None | None |
| 2-Phenoxyethanol | 0.50% | None | None |
| Emercide 1199 Phenoxyethanol (4:1 ratio of 2-Phenoxyethanol + Chloroxylenol) | 0.40% | 0.10% | None |
| 20% Caprylyl Glycol in 2-Phenoxyethanol | 0.40% | None | 0.10% |
| 20% Caprylyl Glycol in Emercide 1199 Phenoxyethanol (4:1 ratio of 2-Phenoxyethnol + Chloroxylenol) | 0.32% | 0.08% | 0.10% |

(Efficacy results for these combinations are shown in Table 1)

B. CTFA Challenge Tests in Personal Care Formulations—Oil in Water Lotion

Procedure: In the initial test in a personal care formulation, various ratios of the components as shown in Table 3, were mixed into a Natural Oil In Water Lotion at 1.0% weight to weight. A standard CTFA cosmetic challenge protocol was followed to assess efficacy against a broad spectrum of microorganisms.

gram negative bacteria and fungi. *S. aureus* was very difficult for any of the preservatives to control in this lotion, and although at 1 week there was some evidence that the addition of caprylyl glycol improved performance, complete eradication of the inoculum was not achieved.

Conclusions: Overall, the addition of caprylyl glycol to the 2-phenoxyethanol/chloroxylenol blend greatly improved activity.

TABLE 3

Concentration Of Each Active Ingredient In Lotion With 1% Addition Of Blend.

| Preservative Blend | Phenoxy-ethanol | Chloroxy-lenol | Caprylyl Glycol |
|---|---|---|---|
| Control - none | None | None | None |
| 3:1 Phenoxyethanol/Chloroxylenol | 0.638% | 0.212% | None |
| 3:1 Phenoxyethanol/Chloroxylenol with 15% Caprylyl Glycol | 0.638% | 0.212% | 0.150% |
| 4:1 Phenoxyethanol/Chloroxylenol | 0.680% | 0.170% | None |
| 4:1 Phenoxyethanol/Chloroxylenol with 15% Caprylyl Glycol | 0.680% | 0.170% | 0.150% |
| 5:1 Phenoxyethanol/Chloroxylenol | 0.708% | 0.142% | None |
| 5:1 Phenoxyethanol/Chloroxylenol with 15% Caprylyl Glycol | 0.708% | 0.142% | 0.150% |
| 4:1 Phenoxyethanol/Chloroxylenol with 20% Caprylyl Glycol | 0.640% | 0.160% | 0.200% |

TABLE 4A

Efficacy Of Preservative Blends With And Without Caprylyl Glycol.

| Preservation Blend (see Table 3 for final concentration) | Colony Forming Units Per Gram Lotion (CFU/g) After 1 Week | | | |
|---|---|---|---|---|
| | P. aeruginosa | S. aureus | C. albicans | A. niger/Penicillium sp. |
| No preservative | $1.2 \times 10^6$ | $4.6 \times 10^6$ | ND* | $1.1 \times 10^4$ |
| 3:1 Phenoxyethanol/Chloroxylenol | $7.5 \times 10^4$ | $1.3 \times 10^6$ | $1.6 \times 10^4$ | $5.8 \times 10^4$ |
| 3:1 Phenoxyethanol/Chloroxylenol with 15% Caprylyl Glycol | $1.0 \times 10^2$ | $8.5 \times 10^5$ | $6.0 \times 10^1$ | $2.5 \times 10^4$ |
| Addition of 15% Caprylyl Glycol to 3:1 blend increased cell reduction by: | 99.9% | 34.6% | 99.6% | 56.9% |
| 4:1 Phenoxyethanol/Chloroxylenol | $3.8 \times 10^4$ | $1.2 \times 10^6$ | $1.6 \times 10^4$ | $2.2 \times 10^4$ |
| 4:1 Phenoxyethanol/Chloroxylenol with 15% Caprylyl Glycol | $1.5 \times 10^2$ | $1.4 \times 10^6$ | $1.0 \times 10^2$ | $2.2 \times 10^4$ |
| Addition of 15% Caprylyl Glycol to 4:1 blend increased cell reduction by: | 96.0% | No increase in reduction | 99.4% | No increase in reduction |
| 4:1 phenoxyethanol/Chloroxylenol with 20% Caprylyl Glycol | $1.3 \times 10^2$ | $1.2 \times 10^6$ | $1.0 \times 10^1$ | $1.8 \times 10^4$ |
| Addition of 20% Caprylyl Glycol to 4:1 blend increased cell reduction by: | 96.6% | No increase in reduction | 99.9% | No increase in reduction |
| 5:1 Phenoxyethanol/Chloroxylenol | $3.6 \times 10^4$ | $1.3 \times 10^6$ | $1.8 \times 10^4$ | $4.7 \times 10^4$ |
| 5:1 Phenoxyethanol/Chloroxylenol with 15% Caprylyl Glycol | $4.0 \times 10^1$ | $8.6 \times 10^4$ | $5.5 \times 10^2$ | $3.0 \times 10^4$ |
| Addition of 15% Caprylyl Glycol to 5:1 blend increased cell reduction by: | 99.9% | 93.4% | 96.9% | 36.2% |

*ND = Not determined

TABLE 4B

Efficacy Of Preservative Blends With And Without Caprylyl Glycol.

| Preservation Blend (see Table 3 for final concentration) | Colony Forming Units Per Gram Lotion (CFU/g) After 2 weeks | | | |
|---|---|---|---|---|
| | P. aeruginosa | S. aureus | C. albicans | A. niger/Penicillium sp. |
| No preservative | $2.3 \times 10^7$ | $4.7 \times 10^7$ | $5.4 \times 10^4$ | $4.1 \times 10^5$ |
| 3:1 Phenoxyethanol/Chloroxylenol | $1.5 \times 10^4$ | $3.2 \times 10^5$ | $1.8 \times 10^3$ | $2.2 \times 10^4$ |
| 3:1 Phenoxyethanol/Chloroxylenol with 15% Caprylyl Glycol | $2.0 \times 10^1$ | $3.7 \times 10^5$ | $<1.0 \times 10^1$ | $2.5 \times 10^3$ |
| Addition of 15% Caprylyl Glycol to 3:1 blend increased cell reduction by: | 99.9% | No increase in reduction | >99.4% | 88.6% |
| 4:1 Phenoxyethanol/Chloroxylenol | $9.3 \times 10^3$ | $4.4 \times 10^5$ | $1.5 \times 10^3$ | $2.5 \times 10^4$ |
| 4:1 Phenoxyethanol/Chloroxylenol with 15% Caprylyl Glycol | $<1.0 \times 10^1$ | $3.3 \times 10^5$ | $<1.0 \times 10^1$ | $3.9 \times 10^3$ |
| Addition of 15% Caprylyl Glycol to 4:1 blend increased cell reduction by: | >99.9% | 25% | >99.3% | 84.4% |
| 4:1 Phenoxyethanol/Chloroxylenol with 20% Caprylyl Glycol | $2.0 \times 10^1$ | $3.7 \times 10^5$ | $<1.0 \times 10^1$ | $5.0 \times 10^2$ |
| Addition of 20% Caprylyl Glycol to 4:1 blend increased cell reduction by: | 99.8% | No increase in reduction | >99.3% | 98.0% |
| 5:1 Phenoxyethanol/Chloroxylenol | $8.7 \times 10^3$ | $4.1 \times 10^5$ | $1.8 \times 10^3$ | $2.1 \times 10^4$ |
| 5:1 Phenoxyethanol/Chloroxylenol with 15% Caprylyl Glycol | $<1.0 \times 10^1$ | $4.3 \times 10^6$ | $<1.0 \times 10^1$ | $1.8 \times 10^4$ |
| Addition of 15% Caprylyl Glycol to 5:1 blend increased cell reduction by: | >99.9% | Decrease in reduction | >99.4 | No increase in reduction |

C. Determination of Minimum Inhibitory Concentrations (MIC's)

Procedure: Stock solutions of Mikrokill PCC and Mikrokill COS were titrated in two-fold serial dilutions in microtiter plate wells containing 0.1 mL of appropriate growth medium. Test strains were grown on agar slants and harvested using standard microbiological techniques. Bacteria were adjusted to one million cells per milliliter in Tryptic Soy Broth. Yeast cells and mold spores were adjusted to one hundred thousand per milliliter in Sabouraud Dextrose Broth. A 0.1 mL volume of organism suspension was added to each test well. The lowest concentration of test compound inhibiting growth was recorded as the Minimum Inhibitory Concentration in Tables 5 and 6, respectively.

TABLE 5

Minimum Inhibitory Concentrations (MIC) for Mikrokill ™ PCC (ppm)

| Organism | ATCC # | Mikrokill ™ PCC (ppm) |
|---|---|---|
| Gram-negative bacteria | | |
| Burkholderia cepacia | 25416 | 625 |
| Escherichia coli | 8739 | 156 |
| Enterobacter gergoviae | 33028 | 2500 |
| Enterobacter aerogenes | 13048 | 310 |
| Flavobacterium odoratum | 13294 | ≦78 |
| Klebsiella pneumoniae | 4352 | 156 |
| Proteus mirabilis | 9240 | 625 |
| Pseudomonas aeruginosa | 9027 | 2500 |
| Gram-positive bacteria | | |
| Staphylococcus aureus | 6538 | 156 |
| Staphylococcus epidermidis | 12228 | 156 |
| Yeast | | |
| Candida albicans | 10231 | ≦78 |
| Saccharomyces cerevisiae | 7752 | ≦78 |
| Mold | | |
| Aspergillus niger | 9642 | ≦78 |
| Penicillium sp. | Cosmetic isolate | ≦78 |

TABLE 6

Minimum Inhibitory Concentrations (MIC) for Mikrokill ™ COS (ppm)

| Organism | ATCC # | Mikrokill ™ COS (ppm) |
|---|---|---|
| Gram-negative bacteria | | |
| Burkholderia cepacia | 25416 | 1250 |
| Escherichia coli | 8739 | 1250 |
| Enterobacter gergoviae | 33028 | 2500 |
| Enterobacter aerogenes | 13048 | 2500 |
| Flavobacterium odoratum | NCIB 13294 | 1250 |
| Klebsiella pneumoniae | 4352 | 1250 |
| Proteus mirabilis | 9240 | 2500 |
| Pseudomonas aeruginosa | 9027 | 2500 |
| Gram-positive bacteria | | |
| Staphylococcus aureus | 6538 | 2500 |
| Staphylococcus epidermidis | 12228 | 2500 |
| Yeast | | |
| Candida albicans | 10231 | 1250 |
| Saccharomyces cerevisiae | 7752 | 2500 |
| Mold | | |
| Aspergillus niger | 9642 | 625 |
| Penicillium sp. | Cosmetic isolate | 625 |

D. CTFA Challenge Tests in Personal Care Formulations—Emulsions and Conditioner

Procedure: The new preservative blend, 4:1 phenoxyethanol:chloroxylenol with 20% caprylyl glycol was mixed into 3 unpreserved, generic, personal care formulations at 0.5% weight to weight. Another new blend, 4:1 phenoxyethanol:chlorphenesin with 20% caprylyl glycol was mixed into 3 unpreserved, generic, personal care formulations (Water in Oil Emulsion, Oil in Water Emulsion and Conditioner) at 1.0% weight to weight. A standard CTFA cosmetic challenge protocol was followed to assess efficacy against a broad spectrum of microorganisms. The four separate inocula were: Staphylococcus aureus (ATCC 6538), Pseudomonas aeruginosa (ATCC 9027), Candida albicans (ATCC 10231), and mixed molds Aspergillus niger (ATCC 6275) and a Penicillium sp. cosmetic isolate. Samples (25 grams each) were inoculated with approximately 2,000,000 bacteria per gram, 50,000 yeast cells per gram or 30,000 mold spores per gram. Individual challenges were prepared from overnight slants of bacteria and yeast cultures and from heavily sporulating mold cultures, 7 to 10 days old. All samples were plated quantitatively for viable organisms after 24 hours and weekly for 3 weeks. Three weeks after the initial challenge, samples were challenged again and the same sampling regime followed.

Results: As shown by the results in Tables 7 to 15B, the new preservative blends demonstrated bactericidal and fungicidal efficacy in several generic cosmetic formulations. Activity of the 4:1 phenoxyethanol:chloroxylenol with 20% caprylyl glycol was best shown in the oil in water emulsion (Tables 9A and 9B) and in the conditioner (Tables 10A and 10B), overall the most susceptible formulation. In the conditioner, all 4 inocula were reduced to <10 cfu/g within 7 days after each challenge. The mixed mold inoculum was more resistant than the other challenges, but was reduced by about 82%-89% within 48 hours. The water in oil emulsion (Tables 8A and 8B) was the least susceptible to microbial contamination, but 24 hour plate counts showed greater reduction in preserved samples than in the unpreserved formulation. Although the bacterial challenge died in the unpreserved samples, sufficient yeast and mold survived to differentiate between preserved and unpreserved material. The 4:1 phenoxyethanol:chlorphenesin with 20% caprylyl glycol preservative was effective against the test bacteria, yeast and molds in all four formulations tested. All preserved formulations showed at least a 99.9% reduction of vegetative bacteria and at least a 90% reduction of yeasts and molds within 7 days following each challenge. Although somewhat slower acting against mold in the Oil in Water Lotion (Table 13A), especially following the first challenge, the reduction in mold counts were >90% within 7 days. Without preservative, molds increased substantially in this formulation.

Conclusions: These preservatives can effectively protect cosmetic formulations against bacterial and fungal growth.

TABLE 7

0.5% 4:1 Phenoxyethanol:Chloroxylenol With 20% Caprylyl Glycol Inoculum Recovered From Controls At '0' Hour - Colony Forming Units Per Gram (Cfu/G).

| Product/Organism | Challenge #1 CFU/g | Challenge #2 CFU/g |
|---|---|---|
| Water in Oil Emulsion | | |
| P. aeruginosa | $2.2 \times 10^6$ | $1.1 \times 10^5$ |
| S. aureus | $9.3 \times 10^5$ | $2.6 \times 10^6$ |
| C. albicans | $9.3 \times 10^3$ | $7.4 \times 10^3$ |
| A. niger + Penicillium sp. | $3.2 \times 10^4$ | $1.8 \times 10^4$ |
| Oil in Water Emulsion | | |
| P. aeruginosa | $6.2 \times 10^6$ | $6.1 \times 10^6$ |
| S. aureus | $1.8 \times 10^6$ | $2.2 \times 10^6$ |
| C. albicans | $5.3 \times 10^3$ | $2.2 \times 10^5$ |
| A. niger + Penicillium sp. | $3.2 \times 10^5$ | $4.9 \times 10^5$ |
| Conditioner | | |
| P. aeruginosa | $5.6 \times 10^6$ | $1.1 \times 10^7$ |
| S. aureus | $1.8 \times 10^6$ | $2.5 \times 10^6$ |
| C. albicans | $4.7 \times 10^4$ | $2.5 \times 10^6$ |
| A. niger. + Penicillium sp. | $3.4 \times 10^5$ | $5.0 \times 10^5$ |

TABLE 8A

Water in Oil Emulsion with 0.5% 4:1 phenoxyethanol:chloroxylenol
with 20% caprylyl glycol.
Preserved Sample Results - Colony Forming Units Per Gram (CFU/G)

| | Challenge #1 | | | | Challenge #2 | | | | |
|---|---|---|---|---|---|---|---|---|---|
| Test Organism | 24 Hours | 7 Days | 14 Days | 21 Days | 24 Hours | 48 Hours | 7 Days | 14 Days | 21 Days |
| P. aeruginosa | <10 | <10 | <10 | <10 | <10 | ND | <10 | <10 | <10 |
| S. aureus | <10 | <10 | <10 | <10 | <10 | ND | <10 | <10 | <10 |
| C. albicans | <10 | <10 | <10 | <10 | $8.2 \times 10^2$ | <10 | <10 | <10 | <10 |
| A. niger + Penicillium sp. | $4.4 \times 10^2$ | <10 | <10 | <10 | $8.2 \times 10^2$ | <10 | <10 | <10 | <10 |

ND = Not determined

TABLE 8B

Unpreserved Water in Oil Emulsion Control Results - Colony Forming Units Per Gram (CFU/G)

| | Challenge #1 | | | | Challenge #2 | | | | |
|---|---|---|---|---|---|---|---|---|---|
| Test Organism | 24 Hours | 7 Days | 14 Days | 21 Days | 24 Hours | 48 Hours | 7 Days | 14 Days | 21 Days |
| P. aeruginosa | $1.5 \times 10$ | <10 | <10 | <10 | $4.0 \times 10^1$ | ND | <10 | <10 | <10 |
| S. aureus | $4.6 \times 10^4$ | <10 | <10 | <10 | $2.9 \times 10^3$ | ND | $1.8 \times 10^4$ | <10 | <10 |
| C. albicans | $2.2 \times 10^3$ | $5.5 \times 10^2$ | $2.5 \times 10^3$ | $6.0 \times 10^1$ | $8.1 \times 10^2$ | ND | $1.5 \times 10^4$ | $2.6 \times 10^3$ | $1.3 \times 10^3$ |
| A. niger + Penicillium sp. | $3.4 \times 10^3$ | $4.5 \times 10^2$ | $1.2 \times 10^3$ | $4.9 \times 10^2$ | $7.5 \times 10^3$ | $4.1 \times 10^3$ | $8.1 \times 10^2$ | $6.1 \times 10^2$ | $2.3 \times 10^3$ |

ND = Not determined

TABLE 9A

Oil in Water Emulsion with 0.5% 4:1 phenoxyethanol:chloroxylenol
with 20% caprylyl glycol.
Preserved Sample Results - Colony Forming Units per Gram (CFU/g).

| | Challenge #1 | | | | Challenge #2 | | | | |
|---|---|---|---|---|---|---|---|---|---|
| Test Organism | 24 Hours | 7 Days | 14 Days | 21 Days | 24 Hours | 48 Hours | 7 Days | 14 Days | 21 Days |
| P. aeruginosa | <10 | <10 | <10 | <10 | <10 | ND | <10 | <10 | <10 |
| S. aureus | <10 | <10 | <10 | <10 | <10 | ND | <10 | <10 | <10 |
| C. albicans | $1.9 \times 10^3$ | <10 | <10 | <10 | $2.1 \times 10^2$ | ND | <10 | <10 | <10 |
| A. niger + Penicillium sp. | $2.3 \times 10^5$ | $<10^3$ | <10 | <10 | $7.6 \times 10^4$ | $2.3 \times 10^4$ | <10 | <10 | <10 |

ND = Not determined

TABLE 9B

Unpreserved Oil in Water Emulsion Control Results - Colony Forming Units per Gram (CFU/g).

| | Challenge #1 | | | | Challenge #2 | | | | |
|---|---|---|---|---|---|---|---|---|---|
| Test Organism | 24 Hours | 7 Days | 14 Days | 21 Days | 24 Hours | 48 Hours | 7 Days | 14 Days | 21 Days |
| P. aeruginosa | $3.0 \times 10^6$ | $1.9 \times 10^4$ | $2.2 \times 10^4$ | $7.1 \times 10^3$ | $4.0 \times 10^6$ | ND | $5.7 \times 10^5$ | $4.3 \times 10^3$ | <10 |
| S. aureus | $1.6 \times 10^6$ | $2.0 \times 10^4$ | $4.0 \times 10^5$ | $4.3 \times 10^4$ | $2.1 \times 10^6$ | ND | $3.0 \times 10^2$ | $3.2 \times 10^4$ | <10 |
| C. albicans | $4.8 \times 10^4$ | $3.8 \times 10^5$ | $4.0 \times 10^5$ | $2.7 \times 10^5$ | $4.6 \times 10^5$ | ND | $2.7 \times 10^6$ | $6.8 \times 10^5$ | $3.6 \times 10^6$ |
| A. niger + Penicillium sp. | $2.2 \times 10^5$ | $1.8 \times 10^5$ | $1.0 \times 10^6$ | $6.9 \times 10^5$ | $7.6 \times 10^4$ | $2.0 \times 10^5$ | $6.1 \times 10^5$ | $2.9 \times 10^5$ | $3.1 \times 10^5$ |

ND = Not determined

Hair Conditioner

TABLE 10A

Conditioner with 0.5% 4:1 phenoxyethanol:chloroxylenol with 20% caprylyl glycol. Preserved Sample Results - Colony Forming Units per Gram (CFU/g).

| Test Organism | Challenge #1 | | | | Challenge #2 | | | | |
|---|---|---|---|---|---|---|---|---|---|
| | 24 Hours | 7 Days | 14 Days | 21 Days | 24 Hours | 48 Hours | 7 Days | 14 Days | 21 Days |
| P. aeruginosa | <10 | <10 | <10 | <10 | <10 | ND | <10 | <10 | <10 |
| S. aureus | <10 | <10 | <10 | <10 | <10 | ND | <10 | <10 | <10 |
| C. albicans | <10 | <10 | <10 | <10 | $1.0 \times 10^3$ | ND | <10 | <10 | <10 |
| A. niger + Penicillium sp. | $1.8 \times 10^5$ | $<10^3$ | <10 | <10 | $1.3 \times 10^5$ | $5.3 \times 10^4$ | <10 | <10 | <10 |

ND = Not determined

TABLE 10B

Unpreserved Conditioner Control Results - Colony Forming Units per Gram (CFU/g)

| Test Organism | Challenge #1 | | | | Challenge #2 | | | | |
|---|---|---|---|---|---|---|---|---|---|
| | 24 Hours | 7 Days | 14 Days | 21 Days | 24 Hours | 48 Hours | 7 Days | 14 Days | 21 Days |
| P. aeruginosa | $3.7 \times 10^6$ | $3.0 \times 10^3$ | $>10^6$ | $1.2 \times 10^5$ | $1.7 \times 10^6$ | ND | $1.9 \times 10^5$ | $2.4 \times 10^5$ | $1.9 \times 10^6$ |
| S. aureus | $2.1 \times 10^6$ | $1.8 \times 10^4$ | $6.5 \times 10^3$ | $1.4 \times 10^5$ | $4.5 \times 10^4$ | ND | Contam* | $>10^6$ | $6.5 \times 10^6$ |
| C. albicans | $3.1 \times 10^6$ | $7.5 \times 10^6$ | $4.9 \times 10^6$ | $3.0 \times 10^6$ | $2.8 \times 10^6$ | ND | $8.0 \times 10^5$ | $4.0 \times 10^5$ | $1.9 \times 10^5$ |
| A. niger + Penicillium sp. | $2.5 \times 10^5$ | $3.9 \times 10^4$ | $2.3 \times 10^5$ | $1.9 \times 10^5$ | $1.4 \times 10^5$ | $2.9 \times 10^5$ | $>10^5$ | $3.1 \times 10^5$ | $4.9 \times 10^5$ |

ND = Not determined

TABLE 11

0.5% 4:1 phenoxyethanol:chlorphenesin with 20% Caprylyl Glycol. Inoculum Recovered From Controls At '0' Hour - Colony Forming Units Per Gram (Cfu/G).

| Product/Organism | Challenge #1 CFU/g | Challenge #2 CFU/g |
|---|---|---|
| Water in Oil Emulsion | | |
| S. aureus | $8.9 \times 10^4$ | $3.8 \times 10^4$ |
| P. aeruginosa + B. cepacia | $1.1 \times 10^5$ | $1.9 \times 10^4$ |
| K. pneumoniae | $1.9 \times 10^5$ | $1.5 \times 10^5$ |
| C. albicans | $4.0 \times 10^3$ | $3.6 \times 10^2$ |
| A. niger + Penicillium sp. | $2.3 \times 10^3$ | $3.8 \times 10^2$ |
| Oil in Water Emulsion | | |
| S. aureus | $1.5 \times 10^6$ | $1.7 \times 10^6$ |
| P. aeruginosa + B. cepacia | $1.5 \times 10^6$ | $8.5 \times 10^6$ |
| K. pneumoniae | $2.0 \times 10^6$ | $1.8 \times 10^6$ |
| C. albicans | $4.4 \times 10^4$ | $1.7 \times 10^5$ |
| A. niger + Penicillium sp. | $3.9 \times 10^5$ | $1.3 \times 10^5$ |
| Conditioner | | |
| S. aureus | $3.1 \times 10^5$ | $5.3 \times 10^4$ |
| P. aeruginosa + B. cepacia | $4.8 \times 10^5$ | $9.2 \times 10^6$ |
| K. pneumoniae | $4.9 \times 10^5$ | $6.0 \times 10^5$ |
| C. albicans | $1.9 \times 10^4$ | $1.3 \times 10^5$ |
| A. niger + Penicillium sp. | $2.6 \times 10^4$ | $2.0 \times 10^4$ |
| Oil in Water Lotion | | |
| S. aureus | $1.8 \times 10^6$ | $1.5 \times 10^6$ |
| P. aeruginosa + B. cepacia | $1.9 \times 10^6$ | $4.7 \times 10^7$ |
| K. pneumoniae | $3.0 \times 10^6$ | $1.1 \times 10^8$ |
| C. albicans | $7.2 \times 10^4$ | $1.2 \times 10^6$ |
| A. niger + Penicillium sp. | $4.5 \times 10^4$ | $8.1 \times 10^5$ |

Water in Oil Emulsion

Table 12A. Water in Oil Emulsion with 1.0% 4:1 phenoxyethanol:chlorphenesin with 20% caprylyl glycol.

Preserved Samples Results—Colony Forming Units per Gram (CFU/g).

TABLE 12A

Water in Oil Emulsion with 1.0% 4:1 phenoxyethanol:chlorphenesin with 20% caprylyl glycol.
Preserved Sample Results - Colony Forming Units per Gram (CFU/g).

| | Challenge #1 | | | | | Challenge #2 | | | | |
|---|---|---|---|---|---|---|---|---|---|---|
| Test Organism | 24 Hours | 48 Hours | 7 Days | 14 Days | 21 Days | 24 Hours | 48 Hours | 7 Days | 14 Days | 21 Days |
| S. aureus | <10 | ND | <10 | <10 | <10 | <10 | ND | <10 | <10 | <10 |
| P. aeruginosa + B. cepacia | <10 | ND | <10 | <10 | <10 | <10 | ND | <10 | <10 | <10 |
| K. pneumoniae | <10 | ND | <10 | <10 | <10 | <10 | ND | <10 | <10 | <10 |
| C. albicans | <10 | ND | <10 | <10 | <10 | <10 | ND | <10 | <10 | <10 |
| A. niger + Penicillium sp. | <10 | <10 | <10 | <10 | <10 | <10 | <10 | <10 | <10 | <10 |

ND = Not determined

TABLE 12B

Unpreserved Water in Oil Emulsion Control Results - Colony Forming Units per Gram (CFU/g).

| | Challenge #1 | | | | | Challenge #2 | | | | |
|---|---|---|---|---|---|---|---|---|---|---|
| Test Organism | 24 Hours | 48 Hours | 7 Days | 14 Days | 21 Days | 24 Hours | 48 Hours | 7 Days | 14 Days | 21 Days |
| S. aureus | $1.1 \times 10^5$ | ND | $1.5 \times 10^2$ | <10 | <10 | $1.4 \times 10^5$ | ND | <10 | <10 | <10 |
| P. aeruginosa + B. cepacia | $5.1 \times 10^4$ | ND | $4.2 \times 10^2$ | <10 | <10 | $8.4 \times 10^3$ | ND | <10 | <10 | <10 |
| K. pneumoniae | $5.2 \times 10^4$ | ND | <10 | <10 | <10 | $5.0 \times 10^3$ | ND | <10 | <10 | <10 |
| C. albicans | $7.0 \times 10^3$ | ND | $3.2 \times 10^2$ | $3.2 \times 10^2$ | $8.1 \times 10^2$ | $4.1 \times 10^3$ | ND | $1.2 \times 10^4$ | $3.1 \times 10^3$ | $5.5 \times 10^3$ |
| A. niger + Penicillium sp. | $1.6 \times 10^3$ | $6.0 \times 10^3$ | $7.0 \times 10^3$ | $2.5 \times 10^2$ | $3.8 \times 10^2$ | $1.7 \times 10^2$ | $3.7 \times 10^3$ | $1.1 \times 10^3$ | $1.7 \times 10^3$ | $3.7 \times 10^2$ |

ND = Not determined

Oil in Water Emulsion

TABLE 13A

Oil in Water Emulsion with 1.0% 4:1 phenoxyethanol:chlorphenesin with 20% caprylyl glycol.
Preserved Sample Results - Colony Forming Units per Gram (CFU/g).

| | Challenge #1 | | | | | Challenge #2 | | | | |
|---|---|---|---|---|---|---|---|---|---|---|
| Test Organism | 24 Hours | 48 Hours | 7 Days | 14 Days | 21 Days | 24 Hours | 48 Hours | 7 Days | 14 Days | 21 Days |
| S. aureus | <10 | ND | <10 | <10 | <10 | <10 | ND | <10 | <10 | <10 |
| P. aeruginosa + B. cepacia | <10 | ND | <10 | <10 | <10 | <10 | ND | <10 | <10 | <10 |
| K. pneumoniae | <10 | ND | <10 | <10 | <10 | <10 | ND | <10 | <10 | <10 |
| C. albicans | <10 | ND | <10 | <10 | <10 | <10 | ND | <10 | <10 | <10 |
| A. niger + Penicillium sp. | $1.1 \times 10^4$ | $1.9 \times 10^3$ | <10 | <10 | <10 | $4.4 \times 10^2$ | <10 | <10 | <10 | <10 |

ND = Not determined

TABLE 13B

Unpreserved Oil in Water Emulsion Control Results - Colony Forming Units per Gram (CFU/g)

| | Challenge #1 | | | | | Challenge #2 | | | | |
|---|---|---|---|---|---|---|---|---|---|---|
| Test Organism | 24 Hours | 48 Hours | 7 Days | 14 Days | 21 Days | 24 Hours | 48 Hours | 7 Days | 14 Days | 21 Days |
| S. aureus | $1.1 \times 10^6$ | ND | $1.4 \times 10^4$ | $1.1 \times 10^3$ | $4.0 \times 10^1$ | $1.2 \times 10^6$ | ND | $3.6 \times 10^3$ | $8.9 \times 10^2$ | <10 |
| P. aeruginosa + B. cepacia | $1.2 \times 10^6$ | ND | $2.8 \times 10^6$ | $9.7 \times 10^5$ | $8.0 \times 10^6$ | $1.5 \times 10^7$ | ND | $9.6 \times 10^6$ | $1.3 \times 10^7$ | $8.2 \times 10^6$ |

TABLE 13B-continued

Unpreserved Oil in Water Emulsion Control Results - Colony Forming Units per Gram (CFU/g)

| Test Organism | Challenge #1 | | | | | Challenge #2 | | | | |
|---|---|---|---|---|---|---|---|---|---|---|
| | 24 Hours | 48 Hours | 7 Days | 14 Days | 21 Days | 24 Hours | 48 Hours | 7 Days | 14 Days | 21 Days |
| K. pneumoniae | $1.6 \times 10^6$ | ND | $1.1 \times 10^5$ | $9.4 \times 10^3$ | $1.5 \times 10^2$ | $3.3 \times 10^5$ | ND | $2.5 \times 10^5$ | $3.5 \times 10^5$ | $3.2 \times 10^5$ |
| C. albicans | $1.7 \times 10^5$ | ND | $2.0 \times 10^5$ | $7.7 \times 10^4$ | $2.7 \times 10^5$ | $2.3 \times 10^5$ | ND | $4.2 \times 10^5$ | $8.9 \times 10^4$ | $7.2 \times 10^4$ |
| A. niger + Penicillium sp. | $3.3 \times 10^4$ | $3.4 \times 10^4$ | $3.3 \times 10^4$ | $4.0 \times 10^4$ | $3.4 \times 10^4$ | $4.2 \times 10^4$ | $5.4 \times 10^4$ | $1.2 \times 10^5$ | $1.1 \times 10^5$ | $7.2 \times 10^4$ |

ND = Not determined

Hair Conditioner

TABLE 14A

Hair Conditioner with 1.0% 4:1 phenoxyethanol:chlorphenesin with 20% caprylyl glycol.
Preserved Sample Results - Colony Forming Units per Gram (CFU/g).

| Test Organism | Challenge #1 | | | | | Challenge #2 | | | | |
|---|---|---|---|---|---|---|---|---|---|---|
| | 24 Hours | 48 Hours | 7 Days | 14 Days | 21 Days | 24 Hours | 48 Hours | 7 Days | 14 Days | 21 Days |
| S. aureus | <10 | ND | <10 | <10 | <10 | <10 | ND | <10 | <10 | <10 |
| P. aeruginosa + B. cepacia | <10 | ND | <10 | <10 | <10 | <10 | ND | <10 | <10 | <10 |
| K. pneumoniae | <10 | ND | <10 | <10 | <10 | <10 | ND | <10 | <10 | <10 |
| C. albicans | <10 | ND | <10 | <10 | <10 | <10 | ND | <10 | <10 | <10 |
| A. niger + Penicillium sp. | $1.8 \times 10^2$ | $3.0 \times 10^1$ | <10 | <10 | <10 | <10 | <10 | <10 | <10 | <10 |

ND = Not determined

TABLE 14B

Unpreserved Conditioner Control Results - Colony Forming Units per Gram (CFU/g).

| Test Organism | Challenge #1 | | | | | Challenge #2 | | | | |
|---|---|---|---|---|---|---|---|---|---|---|
| | 24 Hours | 48 Hours | 7 Days | 14 Days | 21 Days | 24 Hours | 48 Hours | 7 Days | 14 Days | 21 Days |
| S. aureus | $<1 \times 10^3$ | ND | <10 | <10 | <10 | <10 | ND | <10 | <10 | <10 |
| P. aeruginosa + B. cepacia | $4.6 \times 10^5$ | ND | $2.9 \times 10^7$ | $1.9 \times 10^7$ | $1.3 \times 10^7$ | $1.9 \times 10^7$ | ND | $2.8 \times 10^7$ | $>10^7$ | $>10^7$ |
| K. pneumoniae | $6.0 \times 10^3$ | ND | <10 | <10 | <10 | <10 | ND | <10 | <10 | <10 |
| C. albicans | $9.8 \times 10^4$ | ND | $6.9 \times 10^4$ | $2.2 \times 10^5$ | $4.4 \times 10^4$ | $8.9 \times 10^4$ | ND | $3.6 \times 10^5$ | $8.0 \times 10^4$ | $1.4 \times 10^5$ |
| A. niger + Penicillium sp. | $1.4 \times 10^4$ | $3.7 \times 10^4$ | $1.5 \times 10^4$ | $3.5 \times 10^4$ | $1.3 \times 10^4$ | $2.0 \times 10^4$ | $2.2 \times 10^4$ | $1.5 \times 10^4$ | $1.1 \times 10^5$ | $5.9 \times 10^4$ |

ND = Not determined

Oil in Water Lotion

TABLE 15A

Oil in Water Lotion with 1.0% 4:1 phenoxyethanol:chlorphenesin with 20% caprylyl glycol.
Preserved Sample Results - Colony Forming Units per Gram (CFU/g).

| Test Organism | Challenge #1 | | | | | Challenge #2 | | | | |
|---|---|---|---|---|---|---|---|---|---|---|
| | 24 Hours | 48 Hours | 7 Days | 14 Days | 21 Days | 24 Hours | 48 Hours | 7 Days | 14 Days | 21 Days |
| S. aureus | <10 | ND | <10 | <10 | <10 | <10 | ND | <10 | <10 | <10 |
| P. aeruginosa + B. cepacia | <10 | ND | <10 | <10 | <10 | <10 | ND | <10 | <10 | <10 |
| K. pneumoniae | <10 | ND | <10 | <10 | <10 | <10 | ND | <10 | <10 | <10 |
| C. albicans | <10 | ND | <10 | <10 | <10 | <10 | ND | <10 | <10 | <10 |
| A. niger + Penicillium sp. | $1.7 \times 10^4$ | $1.8 \times 10^4$ | $2.0 \times 10^1$ | <10 | <10 | $1.3 \times 10^4$ | $1.7 \times 10^3$ | <10 | <10 | <10 |

ND = Not determined

TABLE 15B

| | Unpreserved Oil in Water Lotion Control Results - Colony Forming Units per Gram (CFU/g). | | | | | | | | | |
|---|---|---|---|---|---|---|---|---|---|---|
| | Challenge #1 | | | | | Challenge #2 | | | | |
| Test Organism | 24 Hours | 48 Hours | 7 Days | 14 Days | 21 Days | 24 Hours | 48 Hours | 7 Days | 14 Days | 21 Days |
| S. aureus | $1.5 \times 10^6$ | ND | $2.3 \times 10^6$ | $3.3 \times 10^4$ | $4.5 \times 10^3$ | $1.1 \times 10^6$ | ND | $7.9 \times 10^6$ | $1.9 \times 10^5$ | $7.9 \times 10^3$ |
| P. aeruginosa + B. cepacia | $3.5 \times 10^6$ | ND | $4.0 \times 10^6$ | $>10^7$ | $2.8 \times 10^7$ | $5.4 \times 10^7$ | ND | $1.2 \times 10^8$ | $2.1 \times 10^8$ | $>10^8$ |
| K. pneumoniae | $3.0 \times 10^6$ | ND | $2.9 \times 10^7$ | $6.6 \times 10^7$ | $7.2 \times 10^7$ | $1.1 \times 10^8$ | ND | $1.6 \times 10^8$ | $1.3 \times 10^8$ | $7.4 \times 10^7$ |
| C. albicans | $6.4 \times 10^4$ | ND | $8.9 \times 10^4$ | $4.8 \times 10^4$ | $4.8 \times 10^4$ | $1.1 \times 10^5$ | ND | $1.2 \times 10^5$ | $>10^6$ | $3.8 \times 10^7$ |
| A. niger + Penicillium sp. | $3.6 \times 10^4$ | $2.8 \times 10^4$ | $2.1 \times 10^5$ | $9.8 \times 10^5$ | $2.2 \times 10^5$ | $1.5 \times 10^6$ | $1.0 \times 10^6$ | $1.5 \times 10^6$ | $2.5 \times 10^6$ | $3.8 \times 10^7$ |

ND = Not determined

E. Tetra-Blend MIC Testing

The Minimum Inhibitory Concentrations (MIC) for a 4-component blend containing 64% by weight 2-phenoxyethanol, 8% by weight chlorphenesin, 8% by weight chloroxylenol, and 20% by weight caprylyl glycol was determined using the same procedures stated above in Part C. The results are shown in Table 16.

TABLE 16

Minimum Inhibitory Concentrations (MIC) for 4-Component Blend.

| Organism | ATCC # | 4-Component Blend (ppm) |
|---|---|---|
| Gram-negative bacteria | | |
| Klebsiella pneumoniae | 4352 | 5000 |
| Pseudomonas aeruginosa | 9027 | 5000 |
| Gram-positive bacteria | | |
| Staphylococcus aureus | 6538 | 5000 |
| Yeast | | |
| Candida albicans | 10231 | ≦0.78 |
| Mold | | |
| Aspergillus niger | 9642 | 156 |

While the invention has been described above with reference to specific embodiments thereof, it is apparent that many changes, modifications, and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A composition having effective preservation activity against P. aeruginosa, E. gingivorae, C. albicans and A. niger comprising 20% by weight caprylyl glycol; 64% by weight 2-phenoxyethanol; and 16% by weight chloroxylenol.

2. A composition having effective preservation activity against P. aeruginosa, E. gingivorae, C. albicans and A. niger comprising 20% by weight caprylyl glycol; 64% by weight 2-phenoxyethanol; and 16% by weight chlorphenesin.

3. A composition having effective preservation activity against P. aeruginosa, E. gingivorae, C. albicans and A. niger comprising caprylyl glycol with a preservative comprising chloroxylenol and 2-phenoxyethanol, wherein the carprylyl glycol component constitutes from about 15% to about 25% by weight, based on the sum of caprylyl glycol plus the preservative in the composition; and wherein and the weight ratio of 2-phenoxyethanol to chloroxylenol is from about 3:1 to about 5:1.

4. The composition of claim 3, wherein the carprylyl glycol component constitutes about 20% by weight based on the sum of caprylyl glycol plus the preservative in the composition.

5. The composition of claim 3, wherein the carprylyl glycol component constitutes about 15% by weight based on the sum of caprylyl glycol plus the preservative in the composition.

6. A topical formulation comprising a composition of claim 3 and additives selected from the group consisting of solvents, surfactants emulsifiers, consistency factors, conditioners, emollients, skin caring ingredients, moisturizers, thickeners, lubricants, fillers, anti-oxidants, other preservatives, active ingredients, fragrances and mixtures thereof.

7. The composition of claim 3 wherein the weight ratio of 2-phenoxyethanol to chloroxylenol is about 4:1.

* * * * *

UNITED STATES PATENT AND TRADEMARK OFFICE
CERTIFICATE OF CORRECTION

| | | |
|---|---|---|
| PATENT NO. | : 7,854,940 B2 | Page 1 of 1 |
| APPLICATION NO. | : 11/224397 | |
| DATED | : December 21, 2010 | |
| INVENTOR(S) | : Diana T. Ciccognani et al. | |

It is certified that error appears in the above-identified patent and that said Letters Patent is hereby corrected as shown below:

In Claim 1, column 22, line 18: please replace "E. gingivorae" with -- E. gergoviae --

In Claim 2, column 22, line 22: please replace "E. gingivorae" with -- E. gergoviae --

In Claim 3, column 22, line 26: please replace "E. gingivorae" with -- E. gergoviae --

Signed and Sealed this

Seventh Day of August, 2012

David J. Kappos
*Director of the United States Patent and Trademark Office*